US012761231B2

(12) United States Patent
Baecher et al.

(10) Patent No.: US 12,761,231 B2
(45) Date of Patent: Oct. 13, 2026

(54) METHOD FOR DETERMINING THE LEVEL OF VITAMIN D AND METABOLITES THEREOF

(71) Applicant: Roche Diagnostics Operations, Inc., Indianapolis, IN (US)

(72) Inventors: Silvia Baecher, Munich (DE); Andrea Geistanger, Munich (DE); Dominik Gruber, Munich (DE); Hans-Peter Josel, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 693 days.

(21) Appl. No.: 18/125,708

(22) Filed: Mar. 23, 2023

(65) Prior Publication Data

US 2023/0251277 A1 Aug. 10, 2023

Related U.S. Application Data

(63) Continuation of application No. PCT/EP2021/076462, filed on Sep. 27, 2021.

(30) Foreign Application Priority Data

Sep. 29, 2020 (EP) .................................... 20199000

(51) Int. Cl.
*G01N 33/82* (2006.01)

(52) U.S. Cl.
CPC .................................. *G01N 33/82* (2013.01)

(58) Field of Classification Search
CPC ..................................................... G01N 33/82
See application file for complete search history.

(56) References Cited

U.S. PATENT DOCUMENTS

| | | | | |
|---|---|---|---|---|
| 7,087,395 | B1 | 8/2006 | Garrity et al. | |
| 8,003,400 | B2 | 8/2011 | Kobold et al. | |
| 2010/0068725 | A1 | 3/2010 | Armbruster et al. | |
| 2010/0285603 | A1* | 11/2010 | Kobold .................. | G01N 33/82 436/131 |
| 2014/0273021 | A1* | 9/2014 | Zielinski ............ | G01N 33/5308 436/501 |

FOREIGN PATENT DOCUMENTS

| | | | |
|---|---|---|---|
| EP | 0036145 | A1 | 9/1981 |
| JP | 2009540275 | A | 11/2009 |
| WO | 02057797 | A2 | 7/2002 |

(Continued)

OTHER PUBLICATIONS

International Preliminary Report on Patentability, The International Bureau of WIPO, International Patent Application No. PCT/EP2021/076462, Mar. 28, 2023, 8 pages.

(Continued)

*Primary Examiner* — Rebecca M Fritchman
(74) *Attorney, Agent, or Firm* — Taft Stettinius & Hollister LLP

(57) ABSTRACT

The present invention relates to a method and the use thereof for determining the level of Vitamin D and metabolites thereof. Further, it is an object of the present invention to provide a kit and the use thereof for determining the level of Vitamin D and metabolites thereof.

13 Claims, 4 Drawing Sheets

(56) References Cited

FOREIGN PATENT DOCUMENTS

WO 2016091755 A1 6/2016

OTHER PUBLICATIONS

Figure 1:
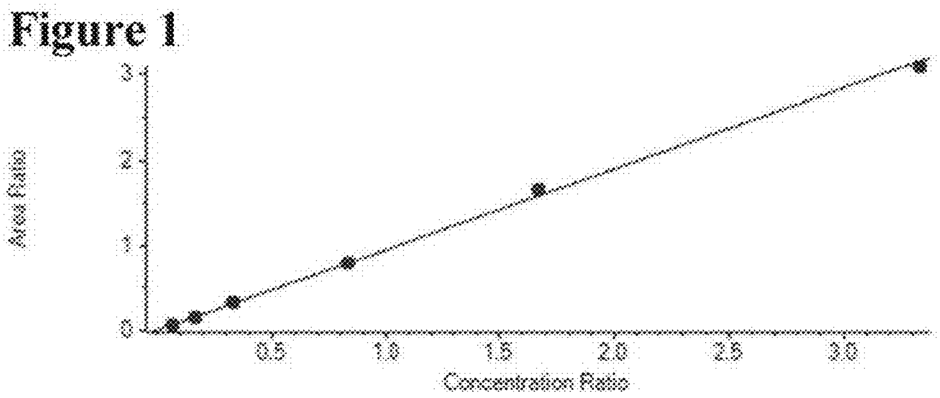

International Search Report; European Patent Office; International Application No. PCT/EP2021/076462; Jan. 18, 2022; 3 pages.
Written Opinion of the International Searching Authority; European Patent Office; International Application No. PCT/EP2021/076462; Jan. 18, 2022; 7 pages.
Varshney, Ankita et al.; Ligand Binding Strategies of Human Serum Albumin: How Can the Cargo be Utilized?; Chirality; 2010; pp. 77-87.
Baecher, Silvia et al.; Simultaneous quantification of four vitamin D metabolites in human serum using high performance liquid chromatography tandem mass spectrometry for vitamin D profiling; Clinical Biochemistry; 2012; pp. 1491-1496; vol. 45.
Japanese Office Action, Japan Patent Office, Japanese Patent Application No. 2023-519272, Jul. 8, 2025, 9 pages.

* cited by examiner

METHOD FOR DETERMINING THE LEVEL OF VITAMIN D AND METABOLITES THEREOF

CROSS-REFERENCE TO RELATED APPLICATIONS

This application is a continuation of International PCT Application No. PCT/EP2021/076462 filed on Sep. 27, 2021, which claims priority to European Patent Application No. 20199000.9 filed on Sep. 29, 2020, the contents of each application are incorporated herein by reference in their entireties.

FIELD OF THE INVENTION

The present invention relates to a method and the use thereof for determining the level of Vitamin D and metabolites thereof. Further, it is an object of the present invention to provide a kit and the use thereof for determining the level of Vitamin D and metabolites thereof.

BACKGROUND OF THE INVENTION

The majority (85%) of Vitamin D metabolites in serum and plasma samples are tightly bound to vitamin D binding protein. To release Vitamin D metabolites from Vitamin D binding protein for subsequent analyte purification and quantification via LC-MS/MS, either protein precipitation via e.g. acetonitril is applied or Salicylic acid Sodium salt is used as release reagent. Vitamin D metabolites, preferably 25-OH-D3, 25-OH-D2, 24R,25(OH)2-D3 in human serum or plasma are quantified applying e.g.

(1) protein precipitation followed by on-line sample preparation and LC-MS/MS (see Clinical Biochemistry 45 (2012) 1491-1496) or (2) an analyte release step using a salicylic acid sodium salt solution followed by immunobead capturing and chemiluminescent detection method (see U.S. Pat. No. 7,087,395 B1).

Salicylate displaces Vitamin D as protein ligand (Varshney et al.: Ligand Binding Strategies of Human Serum Albumin. Chirality, 2010, 22, pp 80-81) and avoids back-binding of Vitamin D to proteins (US 2010/0068725 A1).

Both Vitamin D and salicylic acid are part of MS analyte portfolio, e.g. cobas MS analyte portfolio, which can be measured automatically one after the other.

Therefore, it is highly recommended to avoid salicylic acid sodium salt (sodium salicylate) as potential analyte release reagent (pretreatment) for iVitD assay (iVitD assay means a Vitamin D assays using in a mass spectrometer, preferably a LC-MS based Vitamin D assay) as long as salicylic acid is part of the analyte portfolio, too. There is a risk that residues of iVitD (pre)treatment reagents falsify the result of a subsequent salicylic acid measurement.

Further disadvantages of salicylic acid sodium salt (sodium salicylate) are that the liquid handling (pipetting process) is difficult, because of its high dynamic viscosity (23 mPas at 6° C. for 5.6M solution in 0.01M PBS/methanol 9/1), high consumption is needed and a carry-over risk is produced, because the salt remains on the instrument after a Vitamin D workflow and may falsify a subsequent salicylic acid measurement. A further disadvantage of salicylic acid sodium salt (sodium salicylate) is that this salt has to be applied as a highly concentrated solution in order to reach a satisfying serum:pretreatment volume ratio, preferably in the range of 145:45 to 193:36.

There is thus an urgent need in the art to overcome the above mentioned problems.

It is an object of the present invention to provide a method and the use thereof for for determining the level of Vitamin D and metabolites thereof. Further, it is an object of the present invention to provide a kit and the use thereof for determining the level of Vitamin D and metabolites thereof.

This object is or these objects are solved by the subject matter of the independent claims. Further embodiments are subjected to the dependent claims.

SUMMARY OF THE INVENTION

In the following, the present invention relates to the following aspects:

In a first aspect, the present invention relates to a method for determining the level of Vitamin D and metabolites thereof in a sample comprising:

a) Treating the sample with a releasing reagent, wherein the releasing reagent is provided in an effective level to release Vitamin D and metabolites thereof from a protein or a lipid present in the sample,
   wherein the method is free of the addition of sodium salicylate as the releasing reagent,
   wherein the releasing reagent is a salt comprising
      a benzoate anion.
      one or two hydroxyl groups, which are linked to the phenyl group of the benzoate anion,
      optionally at least one residue having a molar mass of at least 15 g/mol, which is linked to the phenyl group of the benzoate anion,
      a sodium cation or an ammonium cation, or
   wherein the releasing reagent is 3-hydroxybenzoic acid or 2,4-dihydroxybenzoic acid,
b) Optionally purification of the sample obtained from step a), and
c) Determining the level of Vitamin D and metabolites thereof using mass spectrometry.

In a second aspect, the present invention relates to the use of the method of the first aspect of the present invention for determining the level of Vitamin D and metabolites thereof in a sample.

In a third aspect, the present invention relates to a kit for determining the level of Vitamin D and metabolites thereof in a sample, wherein the kit is suitable to perform a method according to the first aspect of the invention comprising
   a releasing reagent, which is provided in an effective level to release Vitamin D and metabolites thereof from a protein or a lipid present in the sample, wherein the kit is free of sodium salicylate as the releasing reagent,
   wherein the releasing reagent is a salt comprising
      a benzoate anion,
      one or two hydroxyl groups, which are linked to the phenyl group of the benzoate anion,
      optionally at least one residue having a molar mass of at least 15 g/mol, which is linked to the phenyl group of the benzoate anion,
      a sodium cation or an ammonium cation, or
   wherein the releasing reagent is 3-hydroxybenzoic acid or 2,4-dihydroxybenzoic acid.

In a fourth aspect, the present invention relates to the use of a kit of the third aspect of the invention in a method according to first aspect of the invention.

LIST OF FIGURES

FIG. 1 shows a calibration curve (area ratio vs. concentration ratio): Calibration is performed by means of LC-MS/

MS of Vitamin D standards in solvent (60% MeOH) containing internal standards as concentrated as in the processed samples.

Figure 5:
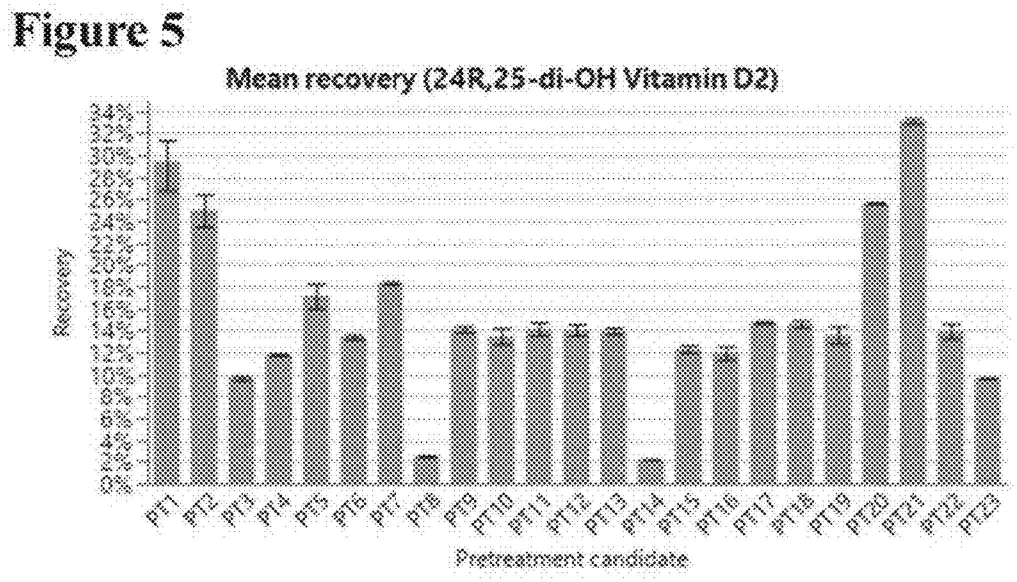

FIGS. 2 to 5 show the recovery of the releasing reagent candidates for 25-OH Vitamin D3 (FIG. 2), 25-OH Vitamin D2 (FIG. 3), 24R25-di-OH Vitamin D3 (FIG. 4) and 24R25-di-OH Vitamin D2 (FIG. 5).

Figure 6:
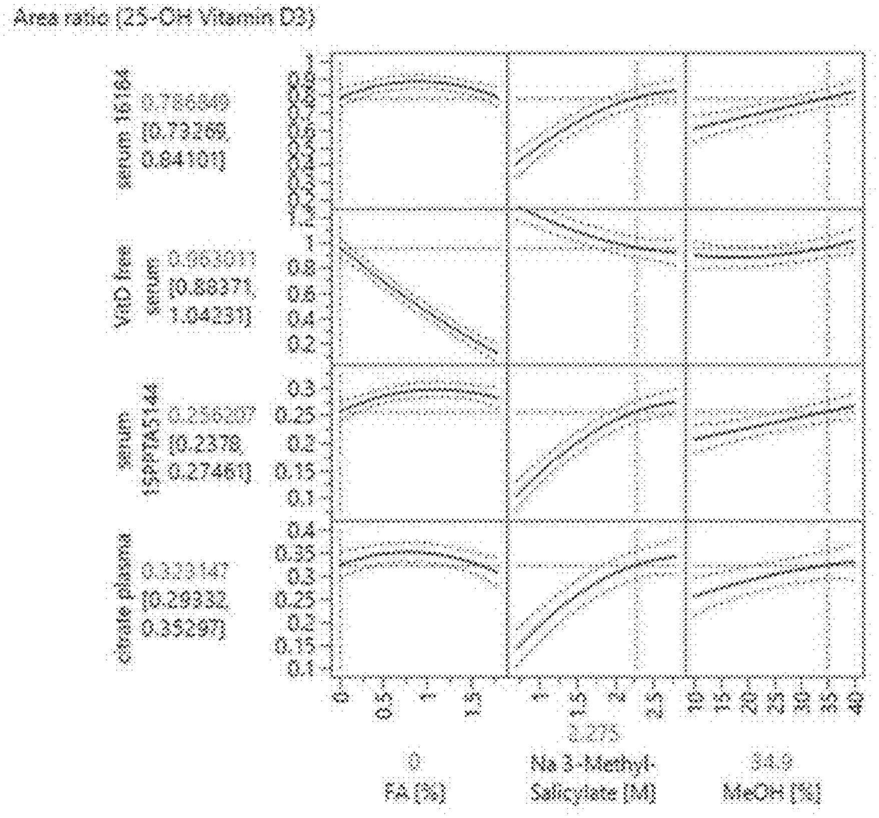

FIG. 6 shows the area ratio of 25-OH Vitamin D3. It is shown the area ratio of 25-OH Vitamin D3 in four different sample types depending on exact pretreatment composition. The setting without pH adjustment (0% FA), with 2.275 M 3-methyl salicylic acid sodium salt and with 35% (v/v) methanol in the solvent is highlighted.

Figure 7A:
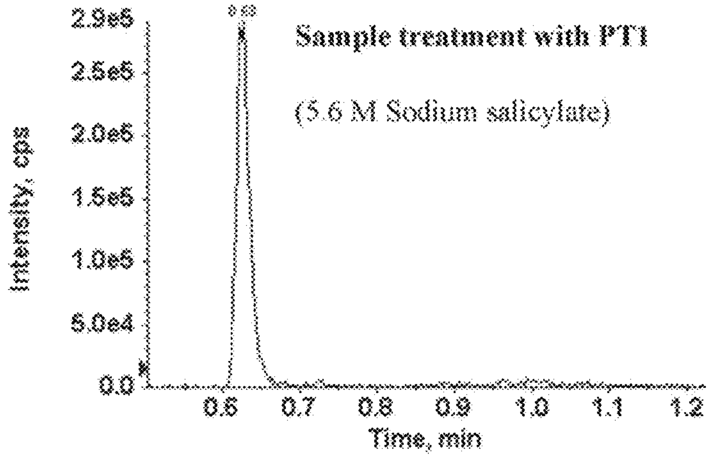
Figure 7B:
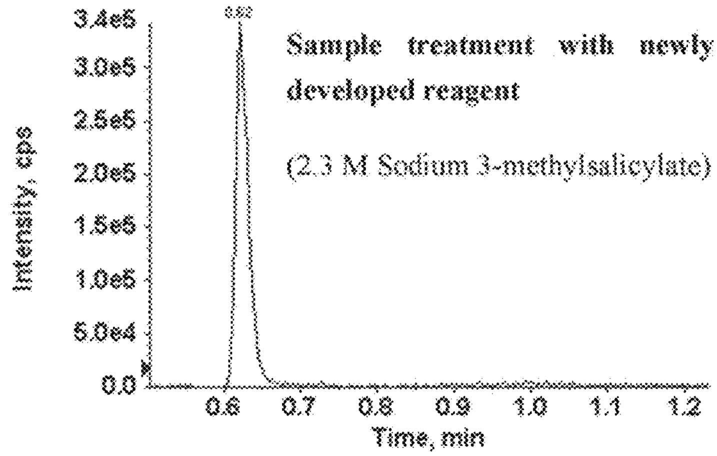

FIGS. 7A and 7B show the intensity as a function of time of 25-OH Vitamin D3 in a patient serum (15PPTA5144), which was treated with 2.3 M sodium 3-methylsalicylate. Chromatograms are shown in order to compare the effects of a sample treatment with PT1 (FIG. 7A) and the newly developed (pre)treatment (FIG. 7B). A mass trace of 25-OH Vitamin D3 is applied.

DETAILED DESCRIPTION OF THE INVENTION

Before the present invention is described in detail below, it is to be understood that this invention is not limited to the particular embodiments and examples described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The various described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Definitions

The word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

Percentages, concentrations, amounts, and other numerical data may be expressed or presented herein in a "range" format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "4% to 20%" should be interpreted to include not only the explicitly recited values of 4% to 20%, but to also include individual values and sub-ranges within the indicated range. Thus, included in this numerical range are individual values such as 4, 5, 6, 7, 8, 9, 10, . . . 18, 19, 20% and sub-ranges such as from 4-10%/a, 5-15%, 10-20%, etc. This same principle applies to ranges reciting minimal or maximal values. Furthermore, such an interpretation should apply regardless of the breadth of the range or the characteristics being described.

The term "about" when used in connection with a numerical value is meant to encompass numerical values within a range having a lower limit that is 5% smaller than the indicated numerical value and having an upper limit that is 5% larger than the indicated numerical value.

The term "determining" the level of Vitamin D and metabolites thereof, as used herein refers to the quantification of Vitamin D and metabolites thereof, e.g. to determining or measuring the level of Vitamin D and metabolites thereof in the sample, employing appropriate methods of detection described elsewhere herein.

In this context "level" or "level value" encompasses the absolute amount, the relative amount or concentration as well as any value or parameter which correlates thereto or can be derived therefrom.

The term "sample" or "patient sample" as used herein refers to a biological sample obtained for the purpose of evaluation in vitro. In the methods of the present invention, the sample or patient sample preferably may comprise any body fluid. The sample can include blood, serum, plasma, urine, saliva, and synovial fluid. Preferred samples are whole blood, serum or plasma. As the skilled artisan will appreciate, any such assessment is made in vitro. The patient sample is discarded afterwards. The patient sample is solely used for the in vitro method of the invention and the material of the patient sample is not transferred back into the patient's body.

The term "Vitamin D and metabolites thereof" means in this context that Vitamin D is used as an umbrella term for several secosteroids found in the human body and essentially consists of or comprises two basic lines: Vitamin D2 and Vitamin D3. Vitamin-D2 and its metabolites are not produced by the body, but with food either medicinal or from fungi. Vitamin D3 is synthesized in large quantities in the body from the precursor molecule 7-dehydrocholesterol under sun/UVB radiation in the skin and is thus the physiological form. By further UV-B irradiation Vitamin D3 again decomposes into inactive metabolites which causes the synthesis process in the skin is self-limiting. The synonym for Vitamin D2 is ergocalciferol, for vitamin D3 cholecalciferol and calciol. Both Vitamin D2 and Vitamin D3 and their metabolites are highly lipophilic and are essential for the transport is bound in plasma to a carrier molecule, the Vitamin D binding protein (DBP, also VDBP). Both molecules are transported to the liver where they are hydroxylated in position 25, it is produced for the Vitamin D3 line calcidiol/calcifediol or 25-OH-Vitamin D/25 hydroxycholecalciferol. This in turn is hydroxylated in the kidney in position 1, whereby the biologically active 1,25 Vitamin D 1,25-dihydroxycholecalciferol, calcitriol, is formed. For the Vitamin D2 line, the corresponding metabolites are called Ercalcidiol/25-hydroxyergocalciferol, Ercalcitriol/1,25-dihydroxyergocalciferol. Preferably, the metabolites of Vitamin D comprises: 25-OH Vitamin D3, 25-OH Vitamin D2, 24R,25(OH)2-Vitamin D3, 24R,25(OH)2-Vitamin D2, 1,25 (OH)2 Vitamin D2 and/or 1,25(OH)2 Vitamin D3:

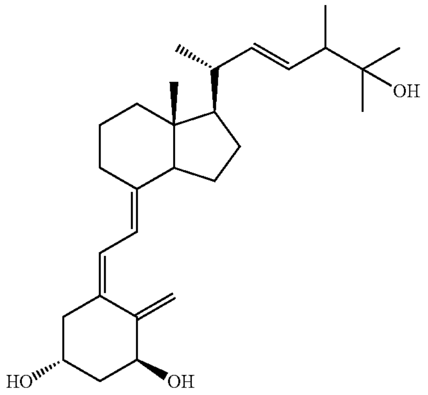

1,25(OH)2
Vitamin D2

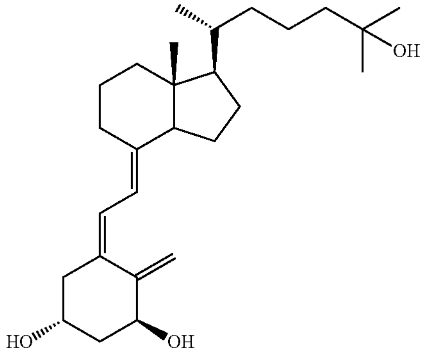

1,25(OH)2
Vitamin D3

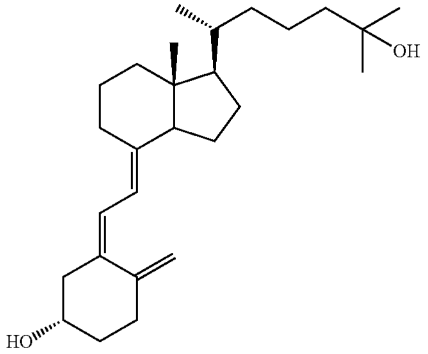

25-OH
Vitamin D3

-continued

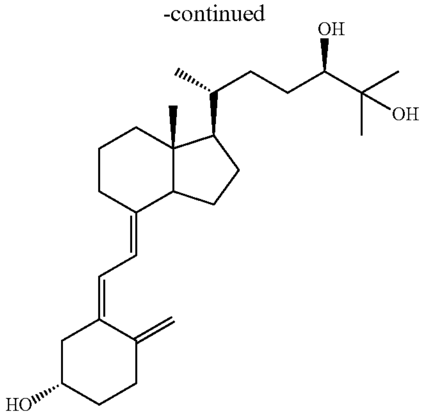

25*R*,25-di-OH
Vitamin D3

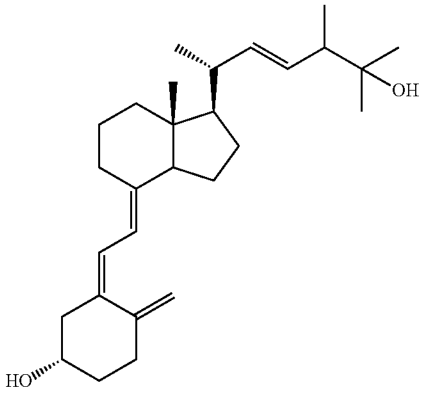

25-OH
Vitamin D2

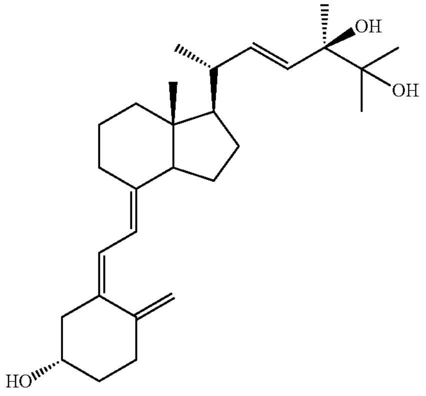

25*R*,25-di-OH
Vitamin D2

Vitamin D and metabolites thereof is/are analyte of interest. Additionally, salicylic acid and salt thereof. e.g. sodium salicylate, can be an analyte of interest. In the context of the present disclosure, the term "analyte", "analyte molecule", or "analyte(s) of interest" are used interchangeably referring the chemical specis to be analysed via mass spectrometry. Chemical specis suitable to be analysed via mass spectrometry, i.e. analytes, can be any kind of molecule present in a living organism, include but are not limited to nucleic acid (e.g. DNA, mRNA, miRNA, rRNA etc.), amino acids, peptides, proteins (e.g. cell surface receptor, cytosolic protein etc.), metabolite or hormones (e.g. testosterone, estrogen, estradiol, etc.), fatty acids, lipids, carbohydrates, steroids, ketosteroids, secosteroids (e.g. Vitamin D), molecules characteristic of a certain modification of another molecule (e.g. sugar moieties or phosphoryl residues on proteins, methyl-residues on genomic DNA) or a substance that has been internalized by the organism (e.g. therapeutic drugs, drugs of abuse, toxin, etc.) or a metabolite of such a substance. Such analyte may serve as a biomarker. In the context of present invention, the term "biomarker" refers to a substance within a biological system that is used as an indicator of a biological state of said system.

In the context of the present disclosure, the term "treating the sample with a releasing reagent" means that the sample and the releasing reagent come together in order to have the possibility to interact, e.g. to react with each other. This can mean that the releasing reagent can be added to the sample or vice versa.

The term "releasing reagent" means in this content a chemical substance, which is capable to release Vitamin D and metabolites thereof from a protein or a lipid. For example, the releasing reagent is suitable to reduce the interaction and/or interference from a protein or a lipid with Vitamin D and metabolites thereof.

The term "effective level of the releasing reagent" means in this content the effective absolute amount, the effective relative amount or effective concentration as well as any effective value or effective parameter which correlates thereto or can be derived therefrom, which is suitable to release the Vitamin D and metabolites thereof from a protein or a lipid. Preferably, at least 10 percent of the bounded Vitamin D and metabolites thereof are released from the protein and/or the lipid.

The term "the method is free of the addition of sodium salicylate as the releasing reagent" means in this content that no sodium salicylate as the releasing reagent is added in the method. Optionally, it can also mean that the method and/or the sample do not comprise any sodium salicylate as the releasing reagent.

The term "releasing reagent is a salt" means in this context that the releasing reagent comprises or consists of two ions—a positively charged ion, the sodium cation or ammonium cation, and a negatively charged ion, the benzoate anion.

Additionally or alternatively, the term "releasing reagent is a salt" means in this context that the releasing reagent is an aqueous salt solution.

The term "benzoate anion" means in this context an negatively charged ion having the following formula:

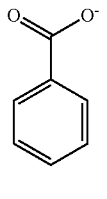

The benzoate anion comprises a phenyl group and a carboxylate anion, which is covalently linked to the phenyl group of the benzoate anion. One or two hydroxyl groups can be additionally linked or bounded to the phenyl group.

The term "protein" means in this context any of a class of nitrogenous organic compounds which have large molecules composed of one or more long chains of amino acids and are an essential part of all living organisms, especially as structural components of body tissues such as muscle, hair, etc., and as enzymes and antibodies. A protein is for example a Vitamin D binding protein or serum albumin.

The term "lipid" means in this context any of a class of organic compounds that are fatty acids or their derivatives and are insoluble in water but soluble in organic solvents. They include many natural oils, waxes, and steroids. The term "lipid" comprises free fatty acids.

The term "Mass Spectrometry" ("Mass Spec" or "MS") or "mass spectrometric determination" or "mass spectrometric analysis" relates to an analytical technology used to identify compounds by their mass. MS is a method of filtering, detecting, and measuring ions based on their mass-to-charge ratio, or "m/z." MS technology generally includes (1) ionizing the compounds to form charged compounds; and (2) detecting the molecular weight of the charged compounds and calculating a mass-to-charge ratio. The compounds may be ionized and detected by any suitable means. A "mass spectrometer" generally includes an ion source and an ion detector. In general, one or more molecules of interest are ionized, and the ions are subsequently introduced into a mass spectrographic instrument where, due to a combination of magnetic and electric fields, the ions follow a path in space that is dependent upon mass ("m") and charge ("z"). The term "ionization" or "ionizing" refers to the process of generating an analyte ion having a net charge equal to one or more units. Negative ions are those having a net negative charge of one or more units, while positive ions are those having a net positive charge of one or more units. The MS method may be performed either in "negative ion mode", wherein negative ions are generated and detected, or in "positive ion mode" wherein positive ions are generated and detected. "After fragmentation by mass spectrometric determination" can mean that e.g. the compound, composition or complex passed through a mass spectrometer and were fragmented.

"Tandem mass spectrometry" or "MS/MS" involves multiple steps of mass spectrometry selection, wherein fragmentation of the analyte occurs in between the stages. In a tandem mass spectrometer, ions are formed in the ion source and separated by mass-to-charge ratio in the first stage of mass spectrometry (MS1). Ions of a particular mass-to-charge ratio (precursor ions or parent ion) are selected and fragment ions (or daughter ions) are created by collision-induced dissociation, ion-molecule reaction, or photodissociation. The resulting ions are then separated and detected in a second stage of mass spectrometry (MS2).

Since a mass spectrometer separates and detects ions of slightly different masses, it easily distinguishes different isotopes of a given element. Mass spectrometry is thus, an important method for the accurate mass determination and characterization of analytes, including but not limited to low-molecular weight analytes, peptides, polypeptides or proteins. Its applications include the identification of proteins and their post-translational modifications, the elucidation of protein complexes, their subunits and functional interactions, as well as the global measurement of proteins in proteomics. De novo sequencing of peptides or proteins by mass spectrometry can typically be performed without prior knowledge of the amino acid sequence.

Most sample workflows in MS further include sample preparation and/or enrichment steps, wherein e.g. the analyte(s) of interest are separated from the matrix using e.g. gas or liquid chromatography. Typically, for the mass spectrometric measurement, the following three steps are performed:

1. a sample comprising an analyte of interest is ionized, usually by complex formation with cations, often by protonation to cations. Ionization source include but are not limited to electrospray ionization (ESI) and atmospheric pressure chemical ionization (APCI).

2. the ions are sorted and separated according to their mass and charge. High-field asymmetric-waveform ion-mobility spectrometry (FAIMS) may be used as ion filter.
3. the separated ions are then detected, e.g. in multiple reaction mode (MRM), and the results are displayed on a chart.

The term "electrospray ionization" or "ESI," refers to methods in which a solution is passed along a short length of capillary tube, to the end of which is applied a high positive or negative electric potential. Solution reaching the end of the tube is vaporized (nebulized) into a jet or spray of very small droplets of solution in solvent vapor. This mist of droplets flows through an evaporation chamber, which is heated slightly to prevent condensation and to evaporate solvent. As the droplets get smaller the electrical surface charge density increases until such time that the natural repulsion between like charges causes ions as well as neutral molecules to be released.

The term "atmospheric pressure chemical ionization" or "APCI," refers to mass spectrometry methods that are similar to ESI; however, APCI produces ions by ion-molecule reactions that occur within a plasma at atmospheric pressure. The plasma is maintained by an electric discharge between the spray capillary and a counter electrode. Then ions are typically extracted into the mass analyzer by use of a set of differentially pumped skimmer stages. A counterflow of dry and preheated Ni gas may be used to improve removal of solvent. The gas-phase ionization in APCI can be more effective than ESI for analyzing less-polar entity.

"High-field asymmetric-waveform ion-mobility spectrometry (FAIMS)" is an atmospheric pressure ion mobility technique that separates gas-phase ions by their behavior in strong and weak electric fields.

"Multiple reaction mode" or "MRM" is a detection mode for a MS instrument in which a precursor ion and one or more fragment ions are selectively detected.

Mass spectrometric determination may be combined with additional analytical methods including chromatographic methods such as gas chromatography (GC), liquid chromatography (LC), particularly HPLC, and/or ion mobility-based separation techniques.

In the context of the present disclosure, the sample may be derived from an "individual" or "subject". Typically, the subject is a mammal. Mammals include, but are not limited to, domesticated animals (e.g., cows, sheep, cats, dogs, and horses), primates (e.g., humans and non-human primates such as monkeys), rabbits, and rodents (e.g., mice and rats).

Before being analysed via Mass Spectrometry, a sample may be treated or pre-treated in a sample- and/or analyte specific manner. In the context of the present disclosure, the term "treatment" or "pre-treatment" refers to any measures required to allow for the subsequent analysis of a desired analyte via mass spectrometry. (Pre-treatment measures typically include but are not limited to the elution of solid samples (e.g. elution of dried blood spots), addition of hemolizing reagent (HR) to whole blood samples, and the addition of enzymatic reagents to urine samples. Also the addition of internal standards (ISTD) is considered as pre-treatment of the sample.

The term "hemolysis reagent" (HR) refers to reagents which lyse cells present in a sample, in the context of this invention hemolysis reagents in particular refer to reagents which lyse the cell present in a blood sample including but not limited to the erythrocytes present in whole blood samples. A well known hemolysis reagent is water ($H_2O$). Further examples of hemolysis reagents include but are not limited to deionized water, liquids with high osmolarity (e.g. 8M urea), ionic liquids, and different detergents.

Typically, an "internal standard" (ISTD) is a known amount of a substance which exhibits similar properties as the analyte of interest when subjected to the mass spectrometric detection workflow (i.e. including any (pre-)treatment, enrichment and actual detection step). Although the ISTD exhibits similar properties as the analyte of interest, it is still clearly distinguishable from the analyte of interest. Exemplified, during chromatographic separation, such as gas or liquid chromatography, the ISTD has about the same retention time as the analyte of interest from the sample. Thus, both the analyte and the ISTD enter the mass spectrometer at the same time. The ISTD however, exhibits a different molecular mass than the analyte of interest from the sample. This allows a mass spectrometric distinction between ions from the ISTD and ions from the analyte by means of their different mass/charge (m/z) ratios. Both are subject to fragmentation and provide daughter ions. These daughter ions can be distinguished by means of their m/z ratios from each other and from the respective parent ions. Consequently, a separate determination and quantification of the signals from the ISTD and the analyte can be performed. Since the ISTD has been added in known amounts, the signal intensity of the analyte from the sample can be attributed to a specific quantitative amount of the analyte. Thus, the addition of an ISTD allows for a relative comparison of the amount of analyte detected, and enables unambiguous identification and quantification of the analyte(s) of interest present in the sample when the analyte(s) reach the mass spectrometer. Typically, but not necessarily, the ISTD is an isotopically labeled variant (comprising e.g. $^{2}H$, $^{13}C$, or $^{15}N$ etc, label) of the analyte of interest.

In addition to the pre-treatment, the sample may also be subjected to one or more enrichment steps. In the context of the present disclosure, the term "first enrichment process" or "first enrichment workflow" refers to an enrichment process which occurs subsequent to the (pre-)treatment of the sample and provides a sample comprising an enriched analyte relative to the initial sample. The first enrichment workflow may comprise chemical precipitation (e.g. using acetonitrile) or the use of a solid phase. Suitable solid phases include but are not limited to Solid Phase Extraction (SPE) cartridges, and beads. Beads may be non-magnetic, magnetic, paramagnetic or supermagnetic. Beads may be coated differently to be specific for the analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores.

In the context of the present disclosure the term "second enrichment process" or "second enrichment workflow" refers to an enrichment process which occurs subsequent to the (pre-)treatment and the first enrichment process of the sample and provides a sample comprising an enriched analyte relative to the initial sample and the sample after the first enrichment process.

The term "chromatography" refers to a process in which a chemical mixture carried by a liquid or gas is separated into components as a result of differential distribution of the chemical entities as they flow around or over a stationary liquid or solid phase.

The term "liquid chromatography" or "LC" refers to a process of selective retardation of one or more components of a fluid solution as the fluid uniformly percolates through a column of a finely divided substance, or through capillary passageways. The retardation results from the distribution of the components of the mixture between one or more stationary phases and the bulk fluid, (i.e., mobile phase), as this fluid moves relative to the stationary phase(s). Methods in which the stationary phase is more polar than the mobile phase (e.g., toluene as the mobile phase, silica as the stationary phase) are termed normal phase liquid chromatography (NPLC) and methods in which the stationary phase is less polar than the mobile phase (e.g., water-methanol mixture as the mobile phase and C18 (octadecylsilyl) as the stationary phase) is termed reversed phase liquid chromatography (RPLC).

"High performance liquid chromatography" or "HPLC" refers to a method of liquid chromatography in which the degree of separation is increased by forcing the mobile phase under pressure through a stationary phase, typically a densely packed column. Typically, the column is packed with a stationary phase composed of irregularly or spherically shaped particles, a porous monolithic layer, or a porous membrane. HPLC is historically divided into two different sub-classes based on the polarity of the mobile and stationary phases. Methods in which the stationary phase is more polar than the mobile phase (e.g., toluene as the mobile phase, silica as the stationary phase) are termed normal phase liquid chromatography (NPLC) and the opposite (e.g., water-methanol mixture as the mobile phase and C18 (octadecylsilyl) as the stationary phase) is termed reversed phase liquid chromatography (RPLC). Micro LC refers to a HPLC method using a column having a narrow inner column diameter, typically below 1 mm, e.g. about 0.5 mm. "Ultra high performance liquid chromatography" or "UHPLC" refers to a HPLC method using a pressure of 120 MPa (17,405 lbf/in2), or about 1200 atmospheres. Rapid LC refers to an LC method using a column having an inner diameter as mentioned above, with a short length<2 cm, e.g. 1 cm, applying a flow rate as mentioned above and with a pressure as mentioned above (Micro LC, UHPLC). The short Rapid LC protocol includes a trapping/wash/elution step using a single analytical column and realizes LC in a very short time<1 min.

Further well-known LC modi include hydrophilic interaction chromatography (HILIC), size-exclusion LC, ion exchange LC, and affinity IC.

LC separation may be single-channel LC or multi-channel LC comprising a plurality of IC channels arranged in parallel. In LC analytes may be separated according to their polarity or log P value, size or affinity, as generally known to the skilled person.

A "kit" is any manufacture (e.g., a package or container) comprising at least one reagent, e.g., a medicament for treatment of a disorder, or a probe for specifically detecting a biomarker gene or protein of the invention. The kit is preferably promoted, distributed, or sold as a unit for performing the methods of the present invention. Typically, a kit may further comprise carrier means being compartmentalised to receive in close confinement one or more container means such as vials, tubes, and the like. In particular, each of the container means comprises one of the separate elements to be used in the method of the first aspect. Kits may further comprise one or more other reagents including but not limited to reaction catalyst. Kits may further comprise one or more other containers comprising further materials including but not limited to buffers, diluents, filters, needles, syringes, and package inserts with instructions for use. A tablet may be present on the container to indicate that the composition is used for a specific application, and may also indicate directions for either in vivo or in vitro use. The computer program code may be provided on a data storage medium or device such as a optical storage medium (e.g., a Compact Disc) or directly on a computer or data processing device. Moreover, the kit may, comprise standard amounts for the acid as described elsewhere herein for calibration purposes.

EMBODIMENTS

In a first aspect, the present invention relates to a method for determining the level of Vitamin D and metabolites thereof in a sample comprising:

a) Treating the sample with a releasing reagent, wherein the releasing reagent is provided in an effective level to release Vitamin D and metabolites thereof from a protein or a lipid present in the sample,
  wherein the method is free of the addition of sodium salicylate as the releasing reagent,
  wherein the releasing reagent is a salt comprising
    a benzoate anion.
    one or two hydroxyl groups, which are linked to the phenyl group of the benzoate anion,
    optionally at least one residue having a molar mass of at least 15 g/mol, which is linked to the phenyl group of the benzoate anion,
    a sodium cation or an ammonium cation, or
  wherein the releasing reagent is 3-hydroxybenzoic acid or 2,4-dihydroxybenzoic acid,
b) Optionally purification of the sample obtained from step a), and
c) Determining the level of Vitamin D and metabolites thereof using mass spectrometry.

According to step (a), the sample is treated with a releasing reagent. The releasing reagent is provided in an effective level to release Vitamin D and metabolites thereof from a protein or a lipid present in the sample. The releasing reagent is a salt comprising a benzoate anion, one or two hydroxyl groups, which are linked to the phenyl group of the benzoate anion, optionally at least one residue having a molar mass of at least 15 g/mol, which is linked to the phenyl group of the benzoate anion, a sodium cation or an ammonium cation, or the releasing reagent is 3-hydroxybenzoic acid or 2,4-dihydroxybenzoic acid.

In embodiments of the first aspect of the present invention, the releasing reagent is selected from the group consisting of sodium 3-methylsalicylate, ammonium salicylate, sodium 3-hydroxybenzoate, 3-hydroxybenzoic acid and 2,4-dihydroxybenzoic acid.

In embodiments of the first aspect of the present invention, the releasing reagent is a salt, which is selected from the group consisting of sodium 3-methylsalicylate, ammonium salicylate and sodium 3-hydroxybenzoate. Preferably, the releasing reagent is sodium 3-methylsalicylate.

In embodiments of the first aspect of the present invention, the releasing reagent has the following formula:

(I)

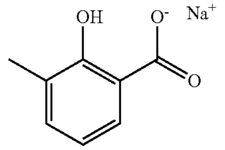

In embodiments of the first aspect of the present invention, the releasing reagent is selected from the following compounds having the following formulae:

(II)

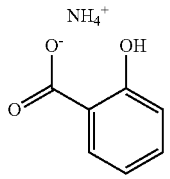

(III)

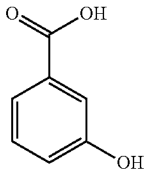

(IV)

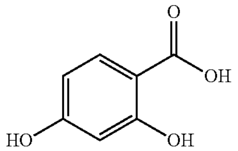

(V)

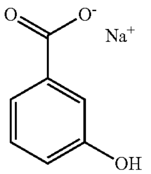

In embodiments of the first aspect of the present invention, the releasing reagent is sodium 3-methylsalicylate having a concentration in the range of 0.7 N to 2.8 M, preferably in the range of 1.5 M to 2.5 M, e.g. 2.0 M.

In embodiments of the first aspect of the present invention, the releasing reagent is ammonium salicylate, preferably having a concentration of 5.6 M.

In embodiments of the first aspect of the present invention, the releasing reagent is sodium 3-hydroxybenzoate, preferably having a concentration of 2.8 M, in embodiments of the first aspect of the present invention, the releasing reagent is 3-hydroxybenzoic acid having a concentration of 0.05 M.

In embodiments of the first aspect of the present invention, the releasing reagent is 2,4-dihydroxybenzoic acid having a concentration of 0.05 M.

In embodiments of the first aspect of the present invention, the releasing reagent is formulated as an ammonium salt or sodium salt. Therefore, the solubility can be in increased in the sample, e.g. serum sample.

In embodiments of the first aspect of the present invention, the releasing reagent is sodium methylsalicylate, e.g sodium 3-methylsalicylate.

In embodiments of the first aspect of the present invention, the releasing reagent is sodium 4-methylsalicylate.

In embodiments of the first aspect of the present invention, the releasing reagent is sodium 5-methylsalicylate.

In embodiments of the first aspect of the present invention, the releasing reagent is sodium 6-methylsalicylate.

In embodiments of the first aspect of the present invention, the releasing reagent is ammonium methylsalicylate.

In embodiments of the first aspect of the present invention, the releasing reagent is ammonium 3-methylsalicylate.

In embodiments of the first aspect of the present invention, the releasing reagent is ammonium 4-methylsalicylate.

In embodiments of the first aspect of the present invention, the releasing reagent is ammonium 5-methylsalicylate.

In embodiments of the first aspect of the present invention, the releasing reagent is ammonium 6-methylsalicylate.

In embodiments of the first aspect of the present invention, the releasing reagent is ammonium hydroybenzoat or sodium hydroxybenzoat.

In embodiments of the first aspect of the present invention, the pH value is adjusted by the addition of an acid, e.g. formic acid. For example, 145 μl serum sample, 45 μl releasing reagent and 10 μl acid are mixed for releasing the Vitamin D and metabolites thereof from the protein or the lipid and to adapt the pH value. Preferably, formic acid is used in a concentration range of 0 to 1.8% (450 mM).

In embodiments of the first aspect of the present invention, formic acid has a concentration in the range of 25 to 450 mM.

In embodiments of the first aspect of the present invention, an acid, e.g. formic acid, is added in step a). Thus, the necessary amount (concentration of the salt solution) of the releasing reagent can be reduced by means of an acid (e.g. formic acid) addition, without a loss in performance. There is a co-action of the releasing reagent and the acid. For example, the following two combinations lead both to a comparable Vitamin D release in a patient serum sample: 450 mM formic acid/0.7 M sodium 3-methylsalicylate and 0 mM formic acid/2.3 M sodium 3-methylsalicylate.

In embodiments of the first aspect of the present invention, the method comprises at least one further step a1) or a2) or both after or before step a):

a1) Coupling of Vitamin D and metabolites thereof obtained from step a) to a solid phase.

a2) Adding an internal standard to the sample. Preferably, the internal standard is added to the sample before step (a). Preferably, the coupling of Vitamin D and metabolites thereof obtained from step a) to a solid phase is performed after step (a).

Suitable solid phases include but are not limited to Solid Phase Extraction (SPE) cartridges, and beads.

In embodiments of the first aspect of the present invention, the bead or beads may be non-magnetic, magnetic, paramagnetic or supermagnetic. Beads may be coated differently to be specific for the analyte of interest. The coating may differ depending on the use intended, i.e. on the intended capture molecule. It is well-known to the skilled person which coating is suitable for which analyte. The beads may be made of various different materials. The beads may have various sizes and comprise a surface with or without pores. For example, Elecsys beads (purchased from Roche Diagnostics) coated with analyte specific antibody can be used as a solid phase in step (a1). Alternatively, for example, other magnetic beads, which bind the antibody covalently, can be used as a solid phase in step (a1).

In embodiments of the first aspect of the present invention, after step (a) and before step (b), the sample is washed in order to remove or at least reduce concentrations of unwanted sample constituents (proteins, lipids), salts (e.g. sodium chloride or 3-methyl salicylic acid sodium salt) or preservatives (e.g. sodium azide, sodium benzoate, oxypyrion, methylisothiazolinone). The washing step can be performed by using water or phosphate buffered saline, e.g. 0.01 M PBS. The described washing step can be followed by a further washing step in order to eluate the magnetic bead from the analyte of interest. The further washing step can be performed by using a solvent, e.g. methanol.

According to optionally step (b), the sample obtained from step a) is purified. The following purification methods or combinations thereof can be used: liquid chromatography, high performance liquid chromatography, hydrophilic interaction chromatography (HILIC), size-exclusion LC, ion exchange LC, affinity LC. In principle, other purification methods are known for the skilled person and can be used to purify the sample. The other known purification methods, e.g. extraction, are thus not explained in detail.

According to step (c), the level of Vitamin D and metabolites thereof using mass spectrometry is determined.

In embodiments of the first aspect of the present invention, the level other analytes of interest than Vitamin D and metabolites thereof can be determined using mass spectrometry, preferably after step (c) or before step (a) of the said method.

In embodiments of the first aspect of the present invention, the level of salicylic acid and salt thereof is determined using mass spectrometry. Preferably, the level of salicylic acid is determined using mass spectrometry. Salicylic acid can be treated in a suitable manner before determining the level of salicylic acids.

In embodiments of the first aspect of the present invention, at least one residue is alkyl, preferably methyl (15 g/mol), ethyl (29 g/mol) or propyl (43 g/mol). In particular, exactly one residue is linked to the phenyl group of the benzoate anion.

More preferably, the residue is linked in position 3, 4 and/or 5 of the phenyl group of the benzoate anion.

In embodiments of the first aspect of the present invention, step (a) comprises additives, wherein the additives are buffer, water and/or alcohol. The buffer can be selected from the following group: phosphate-buffered saline (PBS), ammonium acetate solution, ammonium formate solution. The alcohol can be selected from the following group: methanol, ethanol, 1-propanol, 2-propanol.

Preferably, the buffer is phosphate-buffered saline (PBS).

In embodiments of the first aspect of the present invention, the concentration of PBS is 0.01 M.

Preferably, the alcohol is methanol. For example, the methanol is in the range of 5% to 50% (v/v).

In embodiments of the first aspect of the present invention, the ratio of alcohol to buffer is 5:95 to 40:60 (v/v), preferably 20:80 to 50:50 (v/v), more preferably 35:65 to 40:60 (v/v).

In embodiments of the first aspect of the present invention, the sample is a serum, a plasma or a whole blood sample. For example, if the sample is a whole blood sample an additional separation step, e.g. centrifugation, can be performed.

In embodiments of the first aspect of the present invention, the sample is a human sample.

In embodiments of the first aspect of the present invention, Vitamin D and metabolites thereof are selected from the group consisting of 25-OH Vitamin D3, 25-OH Vitamin D2, 24R,25(OH)2-Vitamin D3, 1,25(OH)2 Vitamin D2, 1,25(OH)2 Vitamin D3 and 24R,25(OH)2-Vitamin D2.

In embodiments of the first aspect of the present invention, the protein is Vitamin D binding protein or albumin, preferably Vitamin D binding protein.

In embodiments of the first aspect of the present invention, the determined level of Vitamin D and metabolites thereof is in the range of 2 to 150 ng/ml for 25-OH Vitamin D3 or 25-OH Vitamin D2.

In embodiments of the first aspect of the present invention, the determined level of Vitamin D and metabolites thereof is in the range of 0.2 to 15 ng/ml for 24R,25(OH)2-Vitamin D3 or 24R,25(OH)2-Vitamin D2.

In embodiments of the first aspect of the present invention, the determined level of Vitamin D and metabolites thereof is in the range of 7-150 pg/ml for 1,25(OH)2 Vitamin D2 or in the range of 7-150 pg/ml for 1,25(OH)2 Vitamin D3.

In embodiments of the first aspect of the present invention, the method is performed automatically. The term "automatically" or "automated" as used herein is a broad term and is to be given its ordinary and customary meaning to a person of ordinary skill in the art and is not to be limited to a special or customized meaning. The term specifically may refer, without limitation, to a process which is performed completely by means of at least one computer and/or computer network and/or machine, in particular without manual action and/or interaction with a user.

In embodiments of the first aspect of the present invention, step b) is performed by chromatography, preferably liquid chromatography (IC) and/or high performance liquid chromatography (HPLC)

In embodiments of the first aspect of the present invention, step c) is performed by using triple quadrupole mass spectrometry.

In embodiments of the first aspect of the present invention, Vitamin D and metabolites thereof is ionized by using electrospray ionisation (ESI).

In a second aspect, the present invention relates to the use of the method of the first aspect of the present invention for determining the level of Vitamin D and metabolites thereof in a sample. All embodiments mentioned for the first aspect of the invention apply for the second aspect of the invention and vice versa.

In a third aspect, the present invention relates to a kit for determining the level of Vitamin D and metabolites thereof in a sample, wherein the kit is suitable to perform a method according to the first aspect of the invention comprising

- a releasing reagent, which is provided in an effective level to release Vitamin D and metabolites thereof from a protein or a lipid present in the sample, wherein the kit is free of sodium salicylate as the releasing reagent,
- wherein the releasing reagent is a salt comprising
  - a benzoate anion.
  - one or two hydroxyl groups, which are linked to the phenyl group of the benzoate anion,
  - optionally at least one residue having a molar mass of at least 15 g/mol, which is linked to the phenyl group of the benzoate anion,
  - a sodium cation or an ammonium cation, or
- wherein the releasing reagent is 3-hydroxybenzoic acid or 2,4-dihydroxybenzoic acid.

All embodiments mentioned for the first aspect of the invention and/or second aspect of the invention apply for the third aspect of the invention and vice versa.

In a fourth aspect, the present invention relates to the use of a kit of the third aspect of the invention in a method according to first aspect of the invention.

All embodiments mentioned for the first aspect of the invention and/or second aspect of the invention and/or third aspect of the invention apply for the fourth aspect of the invention and vice versa.

In embodiments of at least one aspect or all aspects of the present invention, the method of the first aspect of the invention and/or the kit of the third aspect of the present invention is used in a device. Preferably the device is a clinical diagnostic system.

A "clinical diagnostics system" is a laboratory automated apparatus dedicated to the analysis of samples for in vitro diagnostics. The clinical diagnostics system may have different configurations according to the need and/or according to the desired laboratory workflow. Additional configurations may be obtained by coupling a plurality of apparatuses and/or modules together. A "module" is a work cell, typically smaller in size than the entire clinical diagnostics system, which has a dedicated function. This function can be analytical but can be also pre-analytical or post analytical or it can be an auxiliary function to any of the pre-analytical function, analytical function or post-analytical function. In particular, a module can be configured to cooperate with one or more other modules for carrying out dedicated tasks of a sample processing workflow, e.g. by performing one or more pre-analytical and/or analytical and/or post-analytical steps. In particular, the clinical diagnostics system can comprise one or more analytical apparatuses, designed to execute respective workflows that are optimized for certain types of analysis, e.g. clinical chemistry, immunochemistry, coagulation, hematology, liquid chromatography separation, mass spectrometry, etc. Thus the clinical diagnostic system may comprise one analytical apparatus or a combination of any of such analytical apparatuses with respective workflows, where pre-analytical and/or post analytical modules may be coupled to individual analytical apparatuses or be shared by a plurality of analytical apparatuses. In alternative pre-analytical and/or post-analytical functions may be performed by units integrated in an analytical apparatus. The clinical diagnostics system can comprise functional units such as liquid handling units for pipetting and/or pumping and/or mixing of samples and/or reagents and/or system fluids, and also functional units for sorting, storing, transporting, identifying, separating, detecting. The clinical diagnostic system can comprise a sample preparation station for the automated preparation of samples comprising analytes of interest, optionally a liquid chromatography (LC) separation station comprising a plurality of LC channels and/or optionally a sample preparation/LC interface for inputting prepared samples into any one of the LC channels. The clinical diagnostic system can further comprise a controller programmed to assign samples to pre-defined sample preparation workflows each comprising a pre-defined sequence of sample preparation steps and requiring a pre-defined time for completion depending on the analytes of interest. The clinical diagnostic system can further comprise a mass spectrometer (MS) and an LC/MS interface for connecting the LC separation station to the mass spectrometer. The term "automatically" or "automated" as used herein is a broad term and is to be given its ordinary and customary meaning to a person of ordinary skill in the art and is not to be limited to a special or customized meaning. The term specifically may refer, without limitation, to a process which is performed completely by means of at least one computer and/or computer network and/or machine, in particular without manual action and/or interaction with a user.

In embodiments of at least one aspect or all aspects of the present invention, the clinical diagnostic system comprises a sample preparation station.

A "sample preparation station" can be a pre-analytical module coupled to one or more analytical apparatuses or a unit in an analytical apparatus designed to execute a series of sample processing steps aimed at removing or at least reducing interfering matrix components in a sample and/or enriching analytes of interest in a sample. Such processing steps may include any one or more of the following processing operations carried out on a sample or a plurality of samples, sequentially, in parallel or in a staggered manner: pipetting (aspirating and/or dispensing) fluids, pumping fluids, mixing with reagents, incubating at a certain temperature, heating or cooling, centrifuging, separating, filtering, sieving, drying, washing, resuspending, aliquoting, transferring, storing, etc.).

The clinical diagnostic system, e.g. the sample preparation station, may also comprise a buffer unit for receiving a plurality of samples before a new sample preparation start sequence is initiated, where the samples may be individually randomly accessible and the individual preparation of which may be initiated according to the sample preparation start sequence.

The clinical diagnostic system makes use of mass spectrometry more convenient and more reliable and therefore suitable for clinical diagnostics. In particular, high-throughput, e.g. up to 100 samples/hour or more with random access sample preparation and LC separation can be obtained while enabling online coupling to mass spectrometry. Moreover the process can be fully automated increasing the walk-away time and decreasing the level of skills required.

The inventors surprisingly found that the said method can be implemented in the fully automated device, e.g. a cobas i601 analyzer (serum work area solution). This can mean that there is a soft analyte release step followed by immunobead capturing and detection by means of LC-MS/MS.

The inventors could show that in an extensive study 22 reagents have been evaluated for applicability to substitute salicylic acid sodium salt as (pre)treatment within the cobas MS workflow. The results of a first screening study have shown that most reagents do not have any significant release capability and only five reagents have potential release ability. A 3-methylsalicylic acid sodium salt solution seems to be the best choice as it has lead to the highest analyte recovery. In a subsequent comprehensive design of experiment study the 3-methylsalicylic acid sodium salt solution has been optimized and evaluated in detail. It is the most promising (pre)treatment. Applying this reagent high analyte recovery is achieved which is comparable to the recovery with salicylic acid sodium salt. Furthermore, the advantage of 3-methylsalicylic acid sodium salt compared to salicylic acid sodium salt is that this reagent does not interfere with any relevant MRM transition which could result in falsification of salicylic acid results.

In further embodiments, the present invention relates to the following aspects:

1. A method for determining the level of Vitamin D and metabolites thereof in a sample comprising:

a) Treating the sample with a releasing reagent, wherein the releasing reagent is provided in an effective level to release Vitamin D and metabolites thereof from a protein or a lipid present in the sample, wherein the method is free of the addition of sodium salicylate as the releasing reagent, wherein the releasing reagent is a salt comprising a benzoate anion, one or two hydroxyl groups, which are linked to the phenyl group of the benzoate anion, optionally at least one residue having a molar mass of at least 15 g/mol, which is linked to the phenyl group of the benzoate anion, a sodium cation or an ammonium cation, or wherein the releasing reagent is 3-hydroxybenzoic acid or 2,4-dihydroxybenzoic acid, b) Optionally purification of the sample obtained from step a), and c) Determining the level of Vitamin D and metabolites thereof using mass spectrometry.

2. The method of aspect 1, wherein the releasing reagent is selected from the group consisting of sodium 3-methylsalicylate, ammonium salicylate, sodium 3-hydroxybenzoate, 3-hydroxybenzoic acid and 2,4-dihydroxybenzoic acid.

3. The method of aspect 1 or 2, wherein the releasing reagent is a salt, which is selected from the group consisting of sodium 3-methylsalicylate, ammonium salicylate and sodium 3-hydroxybenzoate.

4. The method of any of the proceeding aspects, wherein the releasing reagent is sodium 3-methylsalicylate.

5. The method of any of the proceeding aspects, wherein the at least one residue is alkyl, preferably methyl or ethyl.

6. The method of any of the proceeding aspects, wherein the releasing reagent is sodium 3-methylsalicylate having a concentration in the range of 0.7 M to 2.8 M.

7. The method of any of the proceeding aspects, wherein the releasing reagent is ammonium salicylate, preferably having a concentration of 5.6 M.

8. The method of any of the proceeding aspects, wherein the releasing reagent is sodium 3-hydroxybenzoate, preferably having a concentration of 2.8 M.

9. The method of any of the proceeding aspects, wherein the releasing reagent is 3-hydroxybenzoic acid having a concentration of 0.05 M.

10. The method of any of the proceeding aspects, wherein the releasing reagent is 2,4-dihydroxybenzoic acid having a concentration of 0.05 M.

11. The method of any of the proceeding aspects, wherein the releasing reagent is formulated as an ammonium salt or sodium salt.

12. The method of any of the proceeding aspects, wherein the method comprises at least one further step d) after step c):

d) Determining the level of salicylic acid and salt thereof using mass spectrometry.

13. The method of any of the proceeding aspects, wherein the releasing reagent is sodium methylsalicylate, e.g. sodium 3-methylsalicylate.

14. The method of any of the proceeding aspects, wherein the releasing reagent is sodium 4-methylsalicylate.

15. The method of any of the proceeding aspects, wherein the releasing reagent is sodium 5-methylsalicylate.

16. The method of any of the proceeding aspects, wherein the releasing reagent is sodium 6-methylsalicylate.

17. The method of any of the proceeding aspects, wherein the releasing reagent is ammonium methylsalicylate.

18. The method of any of the proceeding aspects, wherein the releasing reagent is ammonium 3-methylsalicylate.

19. The method of any of the proceeding aspects, wherein the releasing reagent is ammonium 4-methylsalicylate.

20. The method of any of the proceeding aspects, wherein the releasing reagent is ammonium 5-methylsalicylate.

21. The method of any of the proceeding aspects, wherein the releasing reagent is ammonium 6-methylsalicylate.

22. The method of any of the proceeding aspects, wherein the releasing reagent is ammonium hydroybenzoat or sodium hydroxybenzoat.

23. The method of any of the proceeding aspects, wherein the pH value is adjusted e.g. by the addition of an acid, e.g. formic acid.

24. The method of any of the proceeding aspects, wherein formic acid has a concentration in the range of 25 to 450 mM.

25. The method of any of the proceeding aspects, wherein the method comprises at least one further step a1) or a2) or both after or before step a):

a1) Coupling of Vitamin D and metabolites thereof obtained from step a) to a solid phase, a2) Adding an internal standard to the sample.

26. The method of any of the proceeding aspects, wherein step a) comprises additives, wherein the additives are buffer and alcohol.

27. The method of any of the proceeding aspects, wherein the buffer is phosphate-buffered saline (PBS).

28. The method of any of the proceeding aspects, wherein the concentration of PBS is 0.01 M.

29. The method of any of the proceeding aspects, wherein the alcohol is methanol.

30. The method of any of the proceeding aspects, wherein the ratio of alcohol to buffer is 5:95 to 40:60 (v/v), preferably 35:65 to 40:60 (v/v).

31. The method of any of the proceeding aspects, wherein the sample is a serum, a plasma or a whole blood sample.

32. The method of any of the proceeding aspects, wherein the sample is a human sample.

33. The method of any of the proceeding aspects, wherein Vitamin D and metabolites thereof are selected from the group consisting of 25-OH Vitamin D3,25-OH Vitamin D2,24R,25(OH)2-Vitamin D3,1,25(OH)2 Vitamin D2, 1,25 (OH)2 Vitamin D3 and 24R,25(0H)2-Vitamin D2.

34. The method of any of the proceeding aspects, wherein the protein is Vitamin D binding protein or albumin.

35. The method of any of the proceeding aspects, wherein the determined level of Vitamin D and metabolites thereof is in the range of 2 to 150 ng/ml for 25-OH Vitamin D3 or 25-OH Vitamin D2.

36. The method of any of the proceeding aspects, wherein the determined level of Vitamin D and metabolites thereof is in the range of 0.2 to 15 ng/ml for 24R,25(OH)2-Vitamin D3 or 24R,25(OH)2-Vitamin D2.

37. The method of any of the proceeding aspects, wherein the determined level of Vitamin D and metabolites thereof is in the range of 7 to 150 pg/ml for 1,25(OH)2 Vitamin D2 or in the range of 7 to 150 µg/ml for 1,25(OH)2 Vitamin D3.

38. The method of any of the proceeding aspects, wherein the method is performed automatically.

39. The method of any of the proceeding aspects, wherein step b) is performed by chromatography, preferably liquid chromatography (LC) and/or high performance liquid chromatography (HPLC).

40. The method of any of the proceeding aspects, wherein step c) is performed by using triple quadrupole mass spectrometry.

41. The method of any of the proceeding aspects, wherein the Vitamin D and metabolites thereof is ionized by using electrospray ionisation (ESI).

42. Use of the method of any of aspects 1 to 41 for determining the level of Vitamin D and metabolites thereof in a sample.

43. A kit for determining the level of Vitamin D and metabolites thereof in a sample, wherein the kit is suitable to perform a method according to any of the proceeding aspects 1 to 41 comprising a releasing reagent, which is provided in an effective level to release Vitamin D and metabolites thereof from a protein or a lipid present in the sample, wherein the kit is free of sodium salicylate as the releasing reagent, wherein the releasing reagent is a salt comprising
a benzoate anion.
one or two hydroxyl groups, which are linked to the phenyl group of the benzoate anion,
optionally at least one residue having a molar mass of at least 15 g/mol, which is linked to the phenyl group of the benzoate anion,
a sodium cation or an ammonium cation, or
wherein the releasing reagent is 3-hydroxybenzoic acid or 2,4-dihydroxybenzoic acid.

44. Use of a kit of aspect 43 in a method according to any of the proceeding aspects 1 to 41.

EXAMPLES

The following examples are provided to illustrate, but not to limit the presently claimed invention.

Analyte (Vitamin D and Metabolites Thereof) and Internal Standard Materials, Respectively:

24R,25(OH)2-D2 13C5 (Endotherm Life Science Molecules, Saarbrücken)
24R,25(OH)2-D3 13C5 (Endotherm Life Science Molecules, Saarbrücken)
25-OH-D2 13C5 (Endotherm Life Science Molecules, Saarbrücken)
25-OH-D3 13C5 (Endotherm Life Science Molecules, Saarbrücken)
24R,25(OH)2-D2 (Endotherm Life Science Molecules, Saarbrücken)
24R,25(OH)2-D3 (Sigma, Schnelldorf)
25-OH-D2 (Sigma, Schnelldorf)
25-OH-D3 (Sigma, Schnelldorf)

Sample Matrices:

Native serum pool (Roche, Penzberg)
Vitamin D free serum (Golden West Diagnostics, Temecula/USA)
Patient sera and plasma Solvents, Reagent Additives and HPLC Eluent Additive:

Methanol (Biosolve, Valkenswaard/Netherlands)
Formic acid (FA)(VWR, Radnor/USA)
MilliQ water (Merck, Darnstadt)

Ingredients of the Immunobead Suspension:

precoated Elecsys bead suspension (Roche, Penzberg)
Antibody solution (Roche, Penzberg)
0.1 M PBS (Roche, Mannheim)

Chemicals to be Evaluated as Potential Releasing Reagent:

Sodium Salicylate (Sigma. Schnelldorf)
Phenyl Salicylate (Sigma, Schnelldorf)
Diflunisal (Sigma, Schnelldorf)
Ethyl-5-ethoxy-2-hydroxybenzoate (Sigma, Schnelldorf)
Sulfasalazine (Sigma, Schnelldorf)
Methyl Salicylate (Sigma, Schnelldorf)
Aspirin (Sigma, Schnelldorf)
Methyl-4-hydroxybenzoate (Sigma, Schnelldorf)
3-Hydroxybenzoic acid (Sigma, Schnelldorf)
3-Methylsalicylic acid (Sigma, Schnelldorf)
4-Methylsalicylic acid (Sigma, Schnelldorf)
Ethylene glycol monosalicylate (Sigma, Schnelldorf)
Salicylic acid (Sigma, Schnelldorf)
2-Hydroxy-5-methylbenzoic acid (Sigma, Schnelldorf)
2-Methoxy-benzoic acid (Sigma, Schnelldorf)
4-Hydroxyisophthalic acid (Sigma, Schnelldorf)
Methylparaben Sodium (Carbosynth, Newbury/UK)
2,4-Dihydroxybenzoic acid (ABCR, Karlsruhe)
3-Methyl Salicylic acid Sodium salt (ABCR, Kardsruhe)
3-Hydroxybenzoic acid sodium salt (ABCR, Karlsruhe)
2-Hydroxy-4-trifluoromethylbenzoic acid (ABCR, Karlsruhe)
Ammonium Salicylate (ABCR, Karlsruhe)
Sodium chloride (Merck, Darmstadt)

Samples:

0.30 ml di-OH Vitamin D stock solution (0.74 μg/ml 24R,25-di-OH Vitamin D3 and 2.00 μg/ml 24R,25-di-OH Vitamin D2 in methanol) and 0.55 ml mono-OH Vitamin D stock solution (10.00 μg/ml 25-OH Vitamin D3 and 10.00 μg/ml 25-OH Vitamin D2 in methanol) are added to 99.15 ml native serum pool and homogenized Thus resulting concentrations in the spiked pool are:

3.9 ng/mi 24R,25-di-OH Vitamin D3
6.0 ng/mi 24R,25-di-OH Vitamin D2
55.0 ng/ml 25-OH Vitamin D2
84.9 ng/ml 25-OH Vitamin D3

Endogenous amounts in the original native serum pool are taken into account. (According to internal LC-MS/MS results the endogenous amount of 25-OH Vitamin D3 is 19.9 ng/ml. The corresponding value for 24R,25-di-OH Vitamin D3 is approximately 1.9 ng/ml.)

(Pre)Treatment Preparation:

All releasing reagent candidates are dissolved—approximately as concentrated as possible—in methanol/0.01 M PBS 1/9 (v/v). Molar concentrations of the evaluated chemicals are:

| Concentration | potential releasing reagent | abbreviation |
|---|---|---|
| 5.6M | Sodium Salicylate | 'PT1' |
| 0.0009M | Phenyl Salicylate | 'PT17' |
| 0.0004M | Diflunisal | 'PT18' |
| 0.004M | Ethyl-5-ethoxy-2-hydroxybenzoate | 'PT19' |
| 0.009M | Sulfasalazine | 'PT11' |
| 0.01M | Methyl Salicylate | 'PT16' |
| 0.01M | Aspirin | 'PT10' |
| 0.03M | Methyl-4-hydroxybenzoate | 'PT14' |
| 0.05M | 3-Hydroxybenzoic acid | 'PT5' |
| 0.01M | 3-Methylsalicylic acid | 'PT15' |
| 0.02M | 4-Methylsalicylic acid | 'PT6' |
| 0.05M | Ethylen glycol monosalicylat | 'PT3' |
| 0.03M | Salicylic acid | 'PT12' |
| 0.01M | 2-Hydroxy-5-methylbenzoic acid | 'PT13' |
| 0.03M | 2-Methoxy-benzoic acid | 'PT9' |
| 0.001M | 4-Hydroxyisophthalic acid | 'PT4' |
| 1.4M | Methylparaben Sodium | 'PT8' |
| 0.05M | 2,4-Dihydroxybenzoic acid | 'PT7' |
| 1.4M | 3-Methyl Salicylic acid Sodium salt | 'PT21' |
| 2.8M | 3-Hydroxybenzoic acid sodium salt | 'PT20' |
| 0.006M | 2-Hydroxy-4-trifluoromethylbenzoic acid | 'PT22' |
| 5.6M | Ammonium Salicylate | 'PT2' |
| 2.9M | Sodium chloride | 'PT23' |

Molar concentrations of each reagent are chosen depending on solubility. Especially with the sodium and ammonium salts high molar concentrations≥1.4 M are possible, Internal Standard Stock and Working Solution:

The internal standard stock solution (11 μg/ml 24R,25-di-OH Vitamin D3 13C5; 44 μg/ml 25-OH Vitamin D3 13C5; 44 μg/ml 25-OH Vitamin D2 13C5) is prepared in methanol. The internal standard working solution (73 ng/ml 24R,25-di-OH Vitamin D3 13C5; 291 ng/ml 25-OH Vitamin D3 13C5; 291 ng/ml 25-OH Vitamin D2 13C5) is prepared in water/methanol 6/4 (v/v).

Immunobead Suspension:

1507 μl precoated Elecsys bead suspension (21.24 mg/ml) is mixed with 5732 μl 0.01 M PBS and 762 μl antibody solution (1.05 mg/ml). After incubation period of 2 hours at room temperature the immunobead suspension is ready to use.

Sample Preparation:

Sample preparation is implemented on an adjusted automated liquid handling robot (Hamilton, Bonaduz/Switzerland).

10 µl Vitamin D free serum (representing ISTD dummy) are pipetted to 145 µl sample in a plastic vessel. After incubation with periodic shaking for 231 s at 37° C., 45 µl pretreatment reagent are added. Again, an incubation with periodic shaking for 640 s at 37° C. takes place. Therefore Vitamin D should be or is gently released from Vitamin D binding protein. In the next step 50 µl immunobead suspension are pipetted to the mixture. Again, an incubation with periodic shaking for 393 s at 37° C. takes place. After twofold bead wash using 0.01 M PBS and magnetic separation, 60 µl of the elution reagent water/methanol 2/8 (v/v) are added and a 40 s incubation period takes place. It is possible to transfer 40 µl supernatant in a HPLC glass vial while 20 µl have to remain in the vessel to avoid the carry-over of beads into the supernatant. In the final step 40 µl internal standard working solution are added to the supernatant and homogenized by means of sip and spit pipetting technique.

LC-MS/MS:

HPLC-MS % MS analysis is performed using a 1290 Infinity Multisampler and a 1290 Infinity LC System (Agilent Technologies, Santa Clara/USA) coupled to a Triple Quad 6500+MS (Sciex, Darmstadt). 40 µl of each sample are injected on the analytical C18 column (50×2.1 mm, 2.6 µm, Hitachi, Tokio/Japan) in order to separate the analytes. This is realized with a flow rate of 1.0 ml/min and at a column temperature of 50° C. Separation of the analytes is achieved with the following gradient of 50 mM formic acid (A) and methanol (B):

0.00 min: 80% B
0.70 min: 90% B
0.75 min: 98% B
1.70 min: 98% B
1.80 min: 80% B
2.40 min: 80% B The coupled MS detector is operating in positive electrospray ionisation (ESI) mode. The Vitamin D analytes are detected using multi reaction monitoring (MRM) technique. Doing this two periods are applied: 0.00-0.60 min for measurement of 24R,25-di-OH Vitamin D2/D3 and 0.60-2.40 min for the detection of 25-OH Vitamin D2/D3. Ion source settings and MRM parameters are as follows:

| First period: 0.00-0.60 min | |
|---|---|
| Source temperature: | 500° C. |
| Nebulizer gas: | 40 units |
| Heating gas: | 70 units |
| IonSpray voltage: | 3000 V |
| Curtain gas: | 35 units |
| Collision gas: | 10 units |

| Analytes/ internal standards | Parent ion m/z | Product ion m/z | DP | EP | CE | CXP | RT/ min |
|---|---|---|---|---|---|---|---|
| 24R,25(OH)2D3 | 417.3 | 381.2 | 50 | 11 | 12 | 24 | 0.40 |
| | 399.2 | 121.1 | 130 | 11 | 22 | 12 | |
| | 399.2 | 295.2 | 130 | 11 | 22 | 20 | |
| | 381.2 | 295.2 | 140 | 11 | 23 | 25 | |
| 24R,25(OH)2D2 | 393.3 | 268.2 | 145 | 11 | 35 | 14 | 0.45 |
| | 393.3 | 243.2 | 145 | 11 | 15 | 14 | |

-continued

| Analytes/ internal standards | Parent ion m/z | Product ion m/z | DP | EP | CE | CXP | RT/ min |
|---|---|---|---|---|---|---|---|
| | 393.3 | 224.2 | 145 | 11 | 53 | 16 | |
| | 393.3 | 91.1 | 145 | 11 | 95 | 14 | |
| 24R,25(OH)2D3 13C5 | 386.4 | 295.3 | 140 | 11 | 23 | 25 | 0.40 |
| | 404.4 | 295.3 | 130 | 11 | 22 | 20 | |
| | 404.4 | 121.1 | 130 | 11 | 22 | 12 | |
| | 422.4 | 386.4 | 50 | 11 | 12 | 24 | |

DP: Declustering potential, EP: Entrance potential, CE: Collision energy, CXP: Collision cell exit potential, RT: Retention time

| Second period: 0.60-2.40 min | |
|---|---|
| Source temperature: | 500° C. |
| Nebulizer gas: | 60 units |
| Heating gas: | 70 units |
| IonSpray voltage: | 3000 V |
| Curtain gas: | 35 units |
| Collision gas: | 10 units |

| Analytes/ internal standards | Parent ion m/z | Product ion m/z | DP | EP | CE | CXP | RT/ min |
|---|---|---|---|---|---|---|---|
| 25(OH)D3 | 401.3 | 257.2 | 60 | 11 | 20 | 20 | 0.71 |
| | 401.3 | 365.2 | 60 | 11 | 15 | 22 | |
| | 383.3 | 257.2 | 150 | 11 | 18 | 20 | |
| 25(OH)D2 | 413.3 | 395.3 | 60 | 11 | 13 | 24 | 0.75 |
| | 413.3 | 337.3 | 60 | 11 | 15 | 21 | |
| | 413.3 | 159.1 | 60 | 11 | 33 | 15 | |
| 25(OH)D3 13C5 | 406.3 | 370.2 | 60 | 11 | 15 | 22 | 0.71 |
| | 406.3 | 262.2 | 60 | 11 | 20 | 20 | |
| | 388.3 | 262.2 | 150 | 11 | 18 | 20 | |
| 25(OH)D2 13C5 | 418.3 | 400.3 | 60 | 11 | 13 | 24 | 0.75 |
| | 418.3 | 339.2 | 60 | 11 | 15 | 21 | |
| | 418.3 | 159.1 | 60 | 11 | 33 | 15 | |

Calibration is performed by means of LC-MS/MS of Vitamin D standards in solvent (60% MeOH) containing internal standards as concentrated as in the processed samples. For example, calibration levels for 25-OH Vitamin D3 are 2, 5, 10, 25, 50 and 100 ng/ml, while the concentration of 25-OH Vitamin D3 13C5 is set to 30 ng/ml. That results are shown in FIG. 1.

Thus it is possible to determine the mass concentrations of analytes in every processed sample if additionally the correction factor $$\frac{80}{40}\cdot\frac{60}{145}$$

is applied (compensation of changes in analyte concentration during the sample preparation).

Due to the fact that internal standard concentrations are identical both in calibrators and processed samples, it is possible to calculate recoveries for each analyte with the formula:

$$\text{Recovery} = \frac{\text{calculated mass concentration}}{\text{theoretical mass concentration}}\cdot 100\%$$

e.g. for 25-OH Vitamin D3 and PT1:

$$\text{Recovery} = \frac{12.2\ \text{ng/ml}}{84.9\ \text{ng/ml}} \cdot 100\% = 16.3\%$$

The results are shown in FIGS. 2 to 5 show the recovery of the releasing reagent candidates for 25-OH Vitamin D3 (FIG. 2), 25-OH Vitamin D2 (FIG. 3), 24R25-di-OH Vitamin D3 (FIG. 4) and 24R25-di-OH Vitamin D2 (FIG. 5).

Figure 2:
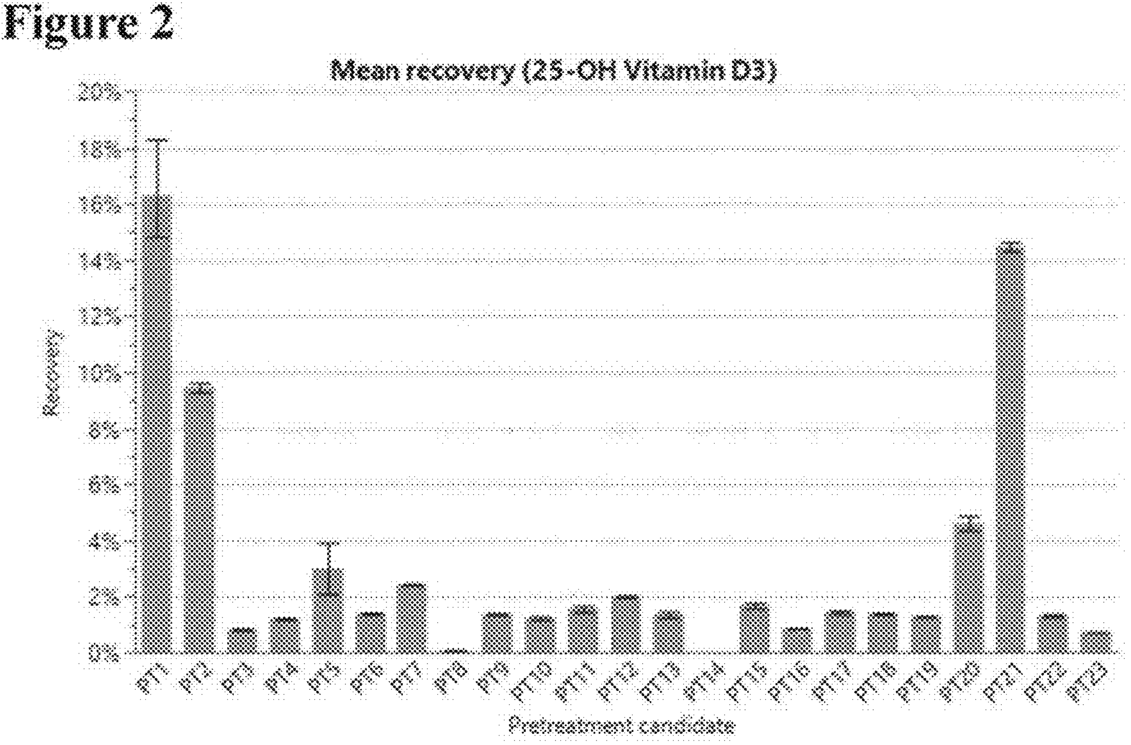
Figure 3:
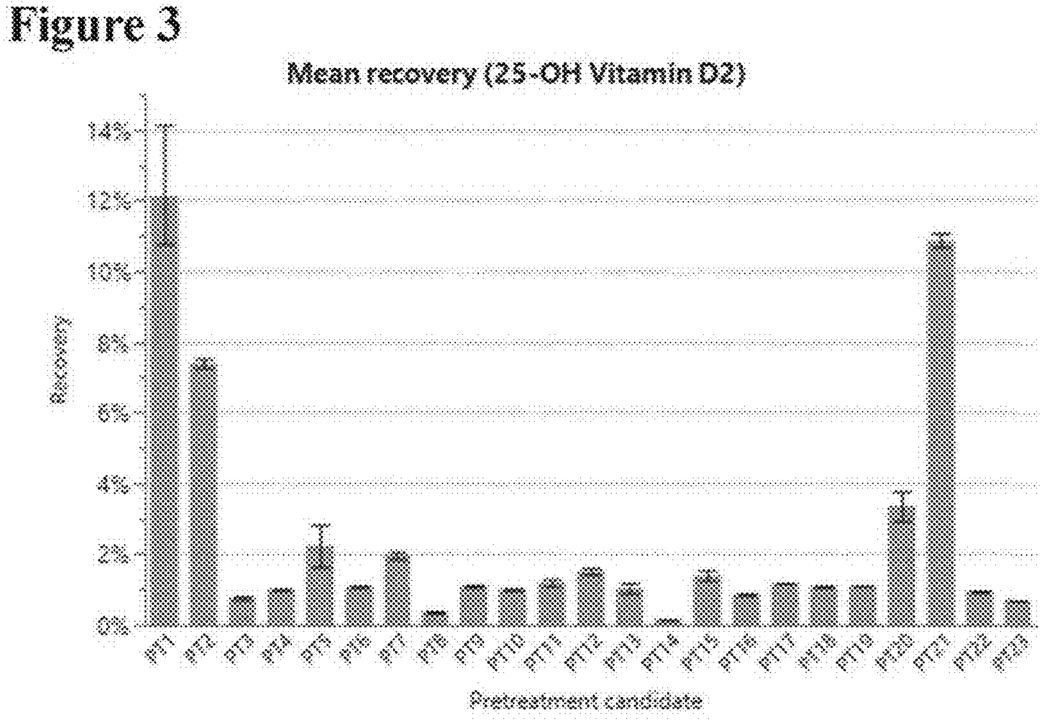
Figure 4:
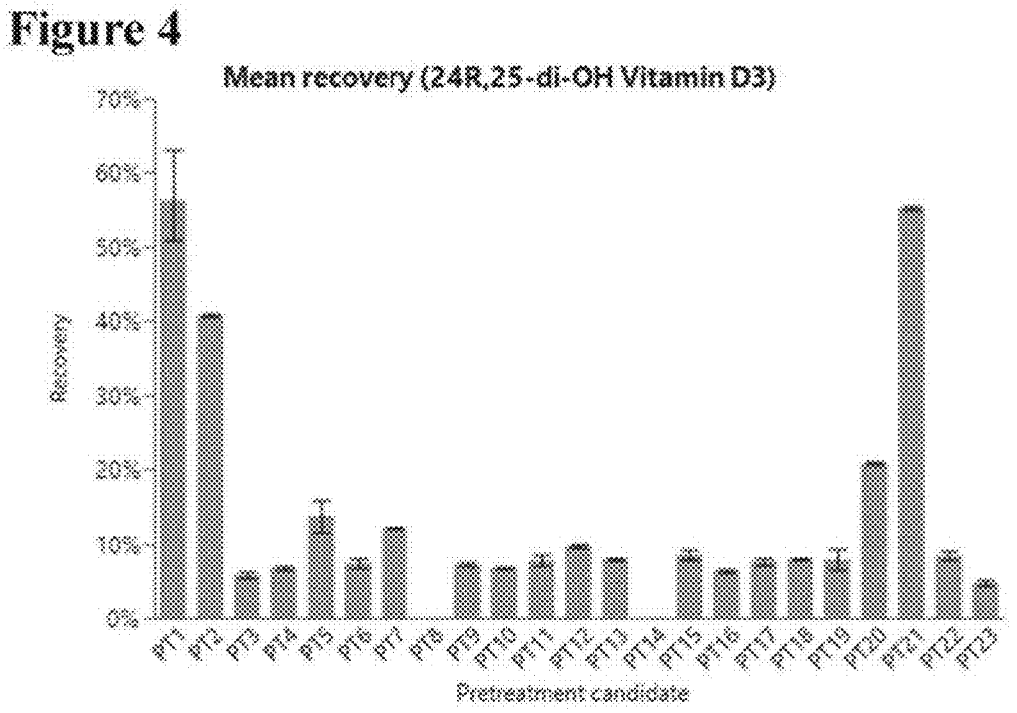

Each error bar in FIGS. 2 and 5 is constructed using the min and the max of the data.

| | |
|---|---|
| PT2 to 23: | two replicates |
| PT1: | four replicates |

Lowest recoveries are achieved by means of PT8 (1.4 M Methylparaben sodium salt) and PT14 (0.03 M Methylparaben). Generally, the group of benzoic acid methyl esters seems to be unsuitable to release Vitamin D and metabolites thereof.

Highest recoveries are accomplished by means of PT1 (5.6 M Sodium Salicylate) followed by PT21 (1.4 M 3-Methylsalicylic acid sodium salt), PT2 (5.6 M Ammonium Salicylate), PT20 (2.8 M 3-Hydroxybenzoic acid sodium salt), PT5 (0.05 M 3-Hydroxybenzoic acid) and PT7 (0.05 M 2,4-Dihydroxybenzoic acid).

PT21 (1.4 M 3-Methylsalicylic acid sodium salt) shows highest analyte recovery, relatively low salt consumption and suitable parent and product ions and is therefore the best choice to replace Salicylic acid in the Vitamin D pretreatment.

Further Pretreatment Optimization in the Frame of 'Design of Experiments' Set-Up (DoE)

Due to preliminary tests the following factors showed highest level of influence and are evaluated in detail regarding analyte recovery:

| Factor | Examined range |
|---|---|
| molar concentration (3-Methylsalicylic acid sodium salt) | 0.7 to 2.8M |
| methanol/0.01M PBS volume ratio | 10/90 to 40/60 (v/v) |
| acidic pH adjustment of serum/plasma by addition of 10 μl | 0.00 to 1.80% FA |

FIG. 6 shows the areas ratio of 25-OH Vitamin D3. As can seen from FIG. 6:

- Acidic pH adjustment does have negative influence on the analyte recovery if a spiked Vitamin D free serum is analyzed. Therefore formic acid (FA) addition is not recommended because this matrix is going to be used in the production of calibrator solutions.
- Optimal recovery results are obtained for all matrices (serum, plasma, Vitamin D free serum) using the following composition:
  - 0% FA (which means: pH adjustment is not necessary)
  - 2.3 M 3-Methylsalicylic acid sodium salt
  - 35/65 (v/v)methanol/0.01 M PBS
- The optimized pretreatment using 2.3 M 3-Methylsalicylic acid sodium salt leads to similar analyte recovery as the pretreatment containing 5.6 M Salicylic acid sodium salt (PT). E.g. for example for patient serum containing 3.8 ng/ml 25-OH Vitamin D3 both chromatograms are illustrated (see FIGS. 7A and 7B).

As can seen from the examples, 2.3 M 3-Methyl Salicylic acid Sodium salt dissolved in 35/65 MeOH/0.01 M PBS (v/v) is the best releasing reagent candidate.

Improvements in comparison to the (pretreatment containing 5.6 M Salicylic acid Sodium salt (PT1) as a releasing reagent are:

- Enhanced pipetting due to lower dynamic viscosity (8.3 mPa·s at 6° C. for 3-methyl salicylic acid Na salt vs. 23 mPa·s at 6C for salicylic acid Na salt)
- Lower consumption of salt, but similar performance (Vitamin D release, circa 18 mg 3-methyl salicylic acid Na salt each sample vs. circa 26 mg salicylic acid Na salt each sample)
- No Carry-Over risk: salicylic acid measurement is independent of a preceding Vitamin D workup This patent application claims the priority of the European patent application 20199000.9, wherein the content of this European patent application is hereby incorporated by references.

The invention claimed is:

1. A method for determining the level of Vitamin D and metabolites thereof in a sample comprising:

a) treating the sample with a releasing reagent, wherein the releasing reagent is provided in an effective level to release Vitamin D and metabolites thereof from a protein or a lipid present in the sample, wherein the method is free of the addition of sodium salicylate as the releasing reagent, wherein the releasing reagent is a salt comprising:

a benzoate anion, one or two hydroxyl groups, which are linked to the phenyl group of the benzoate anion, optionally at least one residue having a molar mass of at least 15 g/mol, which is linked to the phenyl group of the benzoate anion, and a sodium cation or an ammonium cation, or wherein the releasing reagent is 3-hydroxybenzoic acid or 2,4-dihydroxybenzoic acid, b) optionally purification of the treated sample obtained from step a), and c) determining the level of the Vitamin D and metabolites thereof released in step a) using mass spectrometry.

2. The method of claim 1, wherein the releasing reagent is a salt, which is selected from the group consisting of sodium 3-methylsalicylate, ammonium salicylate and sodium 3-hydroxybenzoate.

3. The method of claim 1, wherein the releasing reagent is sodium 3-methylsalicylate.

4. The method of claim 1, wherein the at least one residue is alkyl.

5. The method of claim 1, wherein the releasing reagent is sodium 3-methylsalicylate having a concentration in the range of 0.7 M to 2.8 M.

6. The method of claim 1, wherein the method comprises at least one further step d) after step c):

d) determining A level of salicylic acid and salt thereof using mass spectrometry.

7. The method of claim 1, wherein the method comprises at least one further step a1) or a2) or both after or before step a):

a1) coupling of Vitamin D and metabolites thereof obtained from step a) to a solid phase, a2) adding an internal standard to the sample.

8. The method of claim 1, wherein the releasing reagent in step a) is provided in a solution comprising buffer and alcohol.

9. The method of claim 1, wherein the Vitamin D and metabolites thereof are selected from the group consisting of 25-OH Vitamin D3, 25-OH Vitamin D2, 24R,25(OH)2-Vitamin D3, 1,25(OH)2 Vitamin D2, 1,25(OH)2 Vitamin D3 and 24R,25(OH)2-Vitamin D2.

10. The method of claim 1, wherein the protein is Vitamin D binding protein or albumin.

11. The method of claim 1, wherein the method is performed automatically.

12. The method of claim 1, wherein step b) is performed by chromatography, and wherein step c) is performed by using triple quadrupole mass spectrometry.

13. The method of claim 4, wherein the at least one residue is methyl or ethyl.

* * * * *